July 6, 1937. W. KORDES Plant Pat. 254
ROSE
Filed Dec. 2. 1936
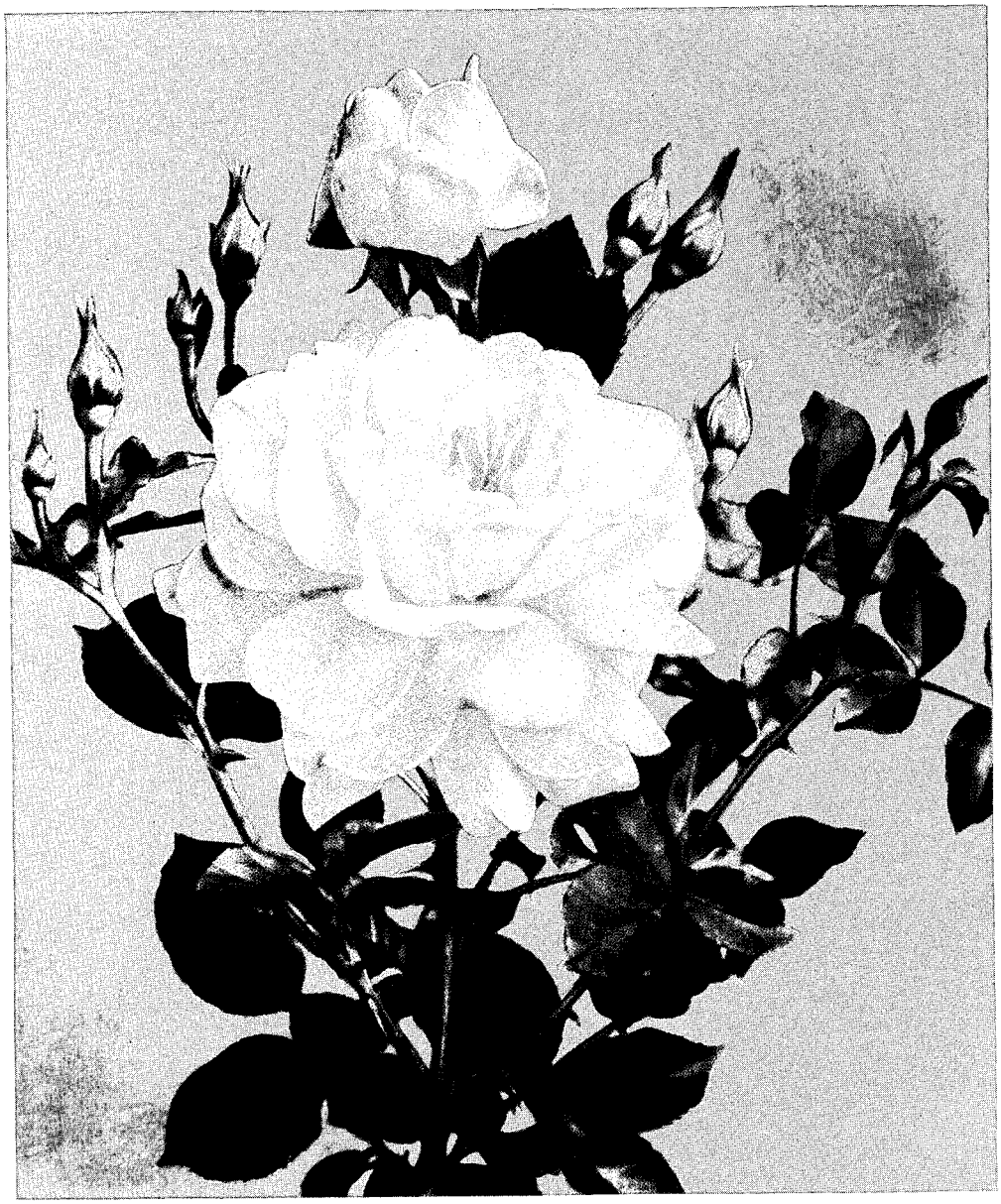
Inventor
Wilhelm Kordes
By Robb & Robb
Attorneys Patented July 6, 1937

Plant Pat. 254

UNITED STATES PATENT OFFICE

254

ROSE

Wilhelm Kordes, Sparrieshoop, Germany, assignor to Jackson & Perkins Company, Newark, N. Y.

Application December 2, 1936, Serial No. 113,922

1 Claim. (Cl. 47—61)

The present invention relates to a new and distinct variety of rose plant having as its primary objective the creation of a new type of decorative or bedding yellow rose. This objective was arrived at by a definite and repeated recrossing within the progeny of Fontanelle (Souvenir of Claudius Pernet x Columbia) x Julien Potin (Souvenir de Claudius Pernet x an unnamed Pernetiana seedling).

In order to produce the result sought and fix the characters, several generations of crosses were necessary, and from each of these in turn those seedlings were selected that came nearest to the ideal decorative or bedding type, cluster habit, fastness of color, and immunity of foliage to diseases.

Generally describing my new origination, the plant in its finished form is vigorous and bushy, the foliage, dark green in color and somewhat crinkled and glossy, being very tough. In order to make certain the satisfactory character of the results, the new variety was subjected to extensive tests over an extended period of time, both in Europe and at varied climatic points of the United States and Canada, and these tests proved it to be practically immune to diseases, particularly black spot and mildew. In this respect alone it is distinctly different from, and an exception among, yellow roses of the Pernetiana strain.

The drawing filed herewith illustrates this new rose, but it is to be understood that owing to the fact that the color of the flower is very original or unusual, it is difficult to describe by color charts and accurately paint or depict. It may be said, however, that in the Gravereaux system it approaches half-way between "saffron" and "gold". Another way of describing this peculiar color is to say that it approximates that of a fresh dandelion in the early morning dew or might also be said to be like burnished brass, so shiny are its petals. A rather important feature resides in the fact that the color is uniform and fades less than that of any other yellow rose.

In respect to its flowering habit, the rose is characterized by its multiple clusters, the initial terminal bloom being quite large with lateral buds, often up to twelve or fifteen, flowering in succession with medium size blooms. The inflorescence is profuse and continuous.

I have asexually reproduced this new rose through the budding and grafting processes and it has always come true to form.

The following is a detailed description of this new variety, reference to color according with the Gravereaux color chart, except where obviously the ordinary dictionary definition is meant:—

Parentage:
*Seed parent.*—Fontanelle.
*Pollen parent.*—Julien Potin.
Classification:
*Botanic.*—Pernetiana.
*Commercial.*—Hybrid tea.

*Flower*

Blooming habit:
Observations made at various places in Germany and in the United States.
Blooms continuous.
Multiple inflorescence.
Bud:
*Size.*—Medium.
*Form.*—Ovoid, unaffected by wet or hot weather.
*Color.*—When sepals first divide—Saffron yellow. When petals begin to unfurl and when half blown—Dandelion yellow or burnished brass.
*Sepals.*—Margin entire, branched, "hood" above bud. Curl back when bloom is half open.
*Calyx.*—Shape—funnel. Size—broad. Aspect—smooth. Odor when rubbed—none.
*Peduncle.*—Length—medium. Aspect—rough. Color — medium green with bronzy tint. Strength—stiff, heavy.
*Opening.*—Bud opens well. Is not affected by adverse conditions.
Bloom:
*Size.*—Terminal blooms very large, side blooms medium. Average size when fully expanded—terminal bloom 4''; side bloom 3''.
*Borne.*—In irregular clusters.
*Stems.*—Long, strong.
*Form.*—When first open—globular. Retains its form to the end.
*Petalage.*—Very double (many petals and stamens hidden). Number of petals under normal conditions varies from fifty to seventy-five.
*Color.*—Uniform. Halfway between Saffron and Gold (Gravereaux). Better described as pure dandelion or burnished brass.
*Variegations.*—None.
*Discoloration.*—First and second days—none. Third day—slightly paler.
Petals:
*Texture.*—Thick, unaffected by wet or hot weather.
*Appearance.*—Inside—shiny. Outside—satiny.
*Form.*—Oval.

*Arrangement.*—Imbricated (regularly arranged shinglelike). Petaloids in center—few, small.

*Persistence.*—Drop off cleanly.

*Fragrance.*—Moderate. Nature—fruity (Russet Apple). Other fragrance—none.

*Lasting quality.*—On plant and as cut flower, very long.

Genital organs:

*Stamens, anthers.*—Small, few. Color—yellow. Arrangement—regular around styles.

*Stamens, filaments (threads).*—Medium. Color—white.

*Pollen.*—Lemon yellow.

*Styles.*—Loosely separated, uneven length. Medium, heavy.

*Stigmas.*—Color—white.

*Ovaries.*—Some protruding from calyx.

Fruit:

Variety is fertile with its own pollen.

*Form.*—Ovoid, pear shaped.

*Aspect.*—Smooth.

*Color at maturity.*—Orange.

*Sepals.*—Caducous (soon falling), recurved.

*Plant*

Form:

Bush.

Growth:

Very vigorous.

Foliage:

*Number of leaflets.*—Generally five, sometimes seven.

*Size.*—Very large.

*Quantity.*—Abundant.

*Color.*—New foliage, upper side—dark green, under side—light green. Old foliage, upper side—dark green, under side—normal green.

*Shape.*—Oval pointed.

*Texture.*—Upper side—glossy, somewhat corrugated. Under side—smooth. Ribs and veins—prominent.

*Edge.*—Serrated (saw toothed).

*Serration.*—Single, small.

*Rachis.*—Color—reddish. Under side—prickles.

*Stipules.*—Medium, smooth.

*Disease resistance.*—Immune.

Wood:

*New wood.*—Color—reddish. Bark—smooth.

*Old wood.*—Color—brown. Bark—smooth.

Thorns: (Thorns are divided into thorns, prickles and short needles.)

*Thorns.*—Quantity—on main stalks from base—ordinary, on laterals from stalk—few. Form—narrow; medium, hooked slightly downward. Color when young—red. Position—irregular.

*Prickles.*—None.

*Short needles.*—None.

The most important characteristics which, in combination, I deem to distinguish my new variety from all other decorative and bedding roses are:

1. The immunity of the foliage from the usual diseases found in yellow roses of the Pernetiana strain;

2. The novel and unusual yellow coloring of the flower;

3. The uniformity of the coloring and lack of tendency of the same to fade; and

4. The large size and number of the flowers growing in multiple clusters.

I claim:

A new and distinct type of decorative or bedding yellow rose plant, characterized by the immunity of its foliage to diseases, the distinctive yellow color of its flower, and the fastness of this color, substantially as shown and described.

WILHELM KORDES.